(12) United States Patent
Pohl et al.

(10) Patent No.: US 10,295,512 B2
(45) Date of Patent: May 21, 2019

(54) MULTI-LUMEN MIXING DEVICE FOR CHROMATOGRAPHY

(71) Applicant: DIONEX CORPORATION, Sunnyvale, CA (US)

(72) Inventors: Christopher A. Pohl, Union City, CA (US); Douglas M. Jamieson, Patterson, CA (US)

(73) Assignee: Dionex Corporation, Sunnyvale, CA (US)

( * ) Notice: Subject to any disclaimer, the term of this patent is extended or adjusted under 35 U.S.C. 154(b) by 62 days.

(21) Appl. No.: 14/963,073

(22) Filed: Dec. 8, 2015

(65) Prior Publication Data

US 2017/0160244 A1  Jun. 8, 2017

(51) Int. Cl.
*G01N 30/34* (2006.01)
*B01D 15/16* (2006.01)
(Continued)

(52) U.S. Cl.
CPC ............. *G01N 30/34* (2013.01); *B01D 15/12* (2013.01); *B01D 15/166* (2013.01);
(Continued)

(58) Field of Classification Search
CPC ....... G01N 2030/027; G01N 2030/347; G01N 30/02; G01N 30/32; G01N 30/34; G01N 30/24; G01N 11/08; G01N 11/06; G01N 30/56; B01F 15/0243; B01F 15/0232; B01F 2005/0005; B01F 5/0456; B01F 9/08; B01F 2009/0063; B01F 7/00391; B01F 7/00966; B01F 13/0035; B01F 7/00275; B01F 13/002; B01D 15/12; B01D 15/166; B01D 15/08; B01L 3/5027; B28C 5/24;
(Continued)

(56) References Cited

U.S. PATENT DOCUMENTS 3,276,751 A   10/1966  Svensson et al.
3,830,369 A   8/1974   Pfadenhauer
(Continued)

FOREIGN PATENT DOCUMENTS

CN   2476022 Y   2/2002
CN   1627067 A   6/2005
(Continued)

OTHER PUBLICATIONS

Dionex Technical Note 108, Reliable Solvent Mixing in UHPLC, copyright 2011, 8 pages.
(Continued)

*Primary Examiner* — John Fitzgerald
*Assistant Examiner* — Truong D Phan
(74) *Attorney, Agent, or Firm* — Timothy J. Ohara

(57) ABSTRACT

A multi-lumen mixing device is described. The multi-lumen mixing device includes a mixer body having an inlet portion and an outlet portion. The multi-lumen mixing device also includes an array of capillary channels within the mixer body, in which each capillary channel has approximately a same length. An inlet for each of the capillaries is proximate to the inlet portion and an outlet for each of the capillaries is proximate to the outlet portion. The array of capillary channels has at least three different cross-sectional areas.

10 Claims, 10 Drawing Sheets

(51) Int. Cl.
  *B01D 15/12* (2006.01)
  *B01F 5/04* (2006.01)
  *B01F 15/02* (2006.01)
  *B01F 5/00* (2006.01)
  *G01N 30/32* (2006.01)

(52) U.S. Cl.
  CPC ........ *B01F 5/0456* (2013.01); *B01F 15/0243* (2013.01); *B01F 2005/0005* (2013.01); *G01N 30/32* (2013.01); *G01N 2030/347* (2013.01)

(58) Field of Classification Search
  CPC .......... F27B 9/24; B01J 2220/54; B01J 20/32; B01J 2220/05
  USPC ........... 73/61.55, 54.05; 366/56, 158.4, 342; 210/198.2, 656; 422/70
  See application file for complete search history.

(56) References Cited

U.S. PATENT DOCUMENTS

| | | | |
|---|---|---|---|
| 3,905,395 | A | 9/1975 | Hupe |
| 4,496,245 | A | 1/1985 | Conrad et al. |
| 4,506,987 | A | 3/1985 | Daughton et al. |
| 4,601,701 | A | 7/1986 | Mueller, Jr. |
| 5,119,669 | A * | 6/1992 | Silvis ..................... G01N 30/10 73/23.35 |
| 5,656,034 | A * | 8/1997 | Kochersperger .......... F04B 9/02 210/656 |
| 5,664,938 | A | 9/1997 | Yang |
| 6,048,496 | A | 4/2000 | Zhou et al. |
| 6,457,855 | B1 * | 10/2002 | Beirau .................. B01F 5/0403 366/336 |
| 7,118,671 | B2 | 10/2006 | Kumakhov et al. |
| 8,511,889 | B2 * | 8/2013 | Choikhet ................ B01F 5/064 138/40 |
| 8,563,325 | B1 * | 10/2013 | Bartsch ............. B01L 3/502776 422/502 |
| 8,979,358 | B2 | 3/2015 | Wiechers |
| 2002/0063060 | A1 * | 5/2002 | Gascoyne ............. B01L 3/5027 204/471 |
| 2003/0165941 | A1 * | 9/2003 | Gjerde ................. B01D 15/366 435/6.12 |
| 2003/0200794 | A1 | 10/2003 | Paul |
| 2005/0226776 | A1 * | 10/2005 | Brady .................. B01J 19/0093 422/400 |
| 2005/0252840 | A1 * | 11/2005 | Arnold .................. B01F 5/0256 210/198.2 |
| 2005/0261470 | A1 * | 11/2005 | Goto ........................ C08J 11/24 528/480 |
| 2006/0289059 | A1 * | 12/2006 | Krylov ................ B01F 13/0072 137/7 |
| 2007/0102362 | A1 * | 5/2007 | Iida ................... B01L 3/502738 210/656 |
| 2010/0097883 | A1 | 4/2010 | Habibi-Naini |
| 2010/0108062 | A1 * | 5/2010 | Ganem ............. A61M 15/0028 128/203.21 |
| 2010/0208543 | A1 * | 8/2010 | Takahashi ........... B01F 13/0071 366/101 |
| 2010/0223922 | A1 * | 9/2010 | McGahee ............... F03B 17/04 60/495 |
| 2011/0061741 | A1 * | 3/2011 | Ingersoll ................. F03D 9/028 137/14 |
| 2011/0188341 | A1 | 8/2011 | Wiechers |
| 2013/0091933 | A1 * | 4/2013 | Tsukada ................. G01N 30/34 73/61.55 |
| 2013/0270478 | A1 | 10/2013 | Wood et al. |
| 2014/0130580 | A1 * | 5/2014 | McAdams ............. G01N 30/00 73/61.52 |
| 2014/0230528 | A1 | 8/2014 | Wang et al. |

FOREIGN PATENT DOCUMENTS

| | | |
|---|---|---|
| CN | 1815221 A | 8/2006 |
| CN | 102309933 A | 1/2012 |
| CN | 104280488 A | 1/2015 |
| EP | 2680957 B1 | 4/2015 |
| WO | 0182996 A2 | 11/2001 |
| WO | 2013187916 A1 | 12/2013 |

OTHER PUBLICATIONS

Eksigent Technical Note, Mixing in Microfluidic Gradient Chromatography Systems, 2003, 2 pages.
GS50 Gradient Pump Operator's Manual, Doc. No. 031612, Rev. 03, Oct. 2003, 162 pages.
Product Manual, Packed-Bed Gradient Mixers, Used on Bionex Gradient Pumps GPM-1, GPM2, AGP and GP40, Doc. No. 034249, Rev. 06, Oct. 20, 2013, 6 pages.
Moskowitz et al., Multicapillary Mixer of Solutions, Science, 1966, 428-429, 153 (3734).

* cited by examiner

MULTI-LUMEN MIXING DEVICE FOR CHROMATOGRAPHY

BACKGROUND

Chromatography is a widely used analytical technique for the chemical analysis and separation of molecules. Chromatography involves the separation of one or more analyte species from other matrix components present in a sample. A stationary phase of a chromatography column is typically selected so that there is an interaction with the analyte. Such interactions can be ionic, hydrophilic, hydrophobic, or combinations thereof. For example, the stationary phase can be derivatized with ionic moieties that ideally will bind to ionic analytes and matrix components with varying levels of affinity. A mobile phase is percolated through the stationary phase and competes with the analyte and matrix components for binding to the ionic moieties. The mobile phase is a term used to describe a liquid solvent or buffer solution that is pumped into a chromatography column inlet. During this competition, the analyte and matrix components will elute off of the stationary phase, preferably at different times, and then be subsequently detected at a detector. Examples of some typical detectors are a conductivity detector, a UV-VIS spectrophotometer, and a mass spectrometer. Over the years, chromatography has developed into a powerful analytical tool that is useful for creating a healthier, cleaner, and safer environment where complex sample mixtures can be separated and analyzed for various industries such as water quality, environmental monitoring, food analysis, pharmaceutical, and biotechnology.

In an effort to improve selectivity, a combination of two or more different mobile phase types can be inputted into the chromatography column where the proportion of mobile phase types changes with time (i.e., gradient elution). For example, a proportion of a stronger eluting mobile phase (e.g., polar organic solvent) can be increased with time to facilitate elution of analyte from the chromatography column. When using two or more different mobile phase types, uniform mixing of the mobile phases can be important for the generation of reproducible peak retention times.

A gradient elution pumping system can deliver varying proportions of mobile phase types as a function of time. In an embodiment, a proportioning pump can be used to draw upon a plurality of different type of mobile phase reservoirs. The proportioning pump can draw from one mobile phase reservoir type for a predetermined time interval and then from a different mobile phase reservoir type for another predetermined time interval. During a single piston cycle, the proportioning pump will output a solvent volume that contains a portion of both mobile phase types. This heterogeneous solvent volume includes a plug of one mobile phase type immediately adjacent to another plug of another mobile phase type. Even though the mobile phase types can be miscible with each other, the outputted heterogeneous solvent volume still requires mixing. In order to achieve reproducible and predictable chromatographic results, the adjoining slugs of mobile phase can be homogeneously mixed prior to being inputted into the separation column.

A mixer can be dynamic where it includes a moving part to homogenize the mobile phase types. However, Applicant believes that such a mechanical device is prone to mechanical failure and wear fragments of such a device may contaminate downstream fluid components possibly compromising performance.

A static mixer where there is no moving part circumvents mechanical failure issues with dynamic mixers. Applicant believes that there is a need for static mixers that have a scalable void volume so that the time resolution of the mixing can be adjusted for a particular gradient elution system. Applicant also believes that there is a need for static mixers that have a relatively fast wash through times and be configured for handling relatively high pressure.

SUMMARY

An embodiment of a method of mixing a heterogeneous solvent volume is described. The heterogeneous solvent volume includes a first plug of a first mobile phase type immediately adjacent to a second plug of a second mobile phase type, where the first mobile phase type and the second mobile phase type are different. The method includes pumping a first mobile phase type and a second mobile phase type with a pump to output the heterogeneous solvent volume. The heterogeneous solvent volume is then inputted into a multi-lumen mixing device that includes a mixer body having an inlet portion and an outlet portion; and an array of capillary channels within the mixer body. Each capillary channel of the array has approximately a same length. An inlet for each of the capillaries is proximate to the inlet portion and an outlet for each of the capillaries is proximate to the outlet portion. The capillary channels of the array have at least three different cross-sectional areas. A mixture is outputted from the multi-lumen mixing device, in which the mixture contains the first mobile phase type and the second mobile phase type. The mixture is then inputted into a chromatography column.

A method of mixing of any of the above embodiments, in which the method further includes separating a sample with the chromatography column; and detecting one or more analytes eluting off of the chromatography column.

A method of mixing of any of the above embodiments, in which the method further includes increasing a proportion of the first mobile phase type with respect to the second mobile phase type as a function of time.

A method of mixing of any of the above embodiments, in which the array of capillary channels has a total volume of equal to or greater than the heterogeneous solvent volume, in which the heterogeneous solvent volume is approximately the volume of one pump cycle.

A method of mixing of any of the above embodiments, in which the array of capillary channels include a first set, a second set, and a third set. The first set corresponding to one or more capillary channels, in which the one or more capillary channels of the first set each have a first cross-sectional area. The second set corresponding to one or more capillary channels, in which the one or more capillary channels of the second set each have a second cross-sectional area. The third set corresponding to one or more capillary channels, in which the one or more capillary channels of the third set each have a third cross-sectional area. A total volume of the first set, the second set, and the third set are approximately equal, where the first cross-sectional area, the second cross-sectional area, and the third cross-sectional area are different.

A method of mixing of any of the above embodiments, in which of capillary channels have a tubular shape.

A method of mixing of any of the above embodiments, in which the pump is a proportioning pump. The proportioning pump being configured to input a first mobile phase type from a first reservoir and to input a second mobile phase type from a second reservoir.

A method of mixing of any of the above embodiments, in which the multi-lumen mixing device is either downstream or upstream of a sample injector.

A multi-lumen mixing device including a mixer body having an inlet portion and an outlet portion; and an array of capillary channels within the mixer body. Each capillary channel has approximately a same length. An inlet for each of the capillaries is proximate to the inlet portion and an outlet for each of the capillaries is proximate to the outlet portion. The capillary channels of the array have at least three different cross-sectional areas. The array of capillary channels includes a first set, a second set, and a third set. The first set corresponding to one or more capillary channels, in which the one or more capillary channels of the first set each have a first cross-sectional area. The second set corresponding to one or more capillary channels, in which the one or more capillary channels of the second set each have a second cross-sectional area. The third set corresponding to one or more capillary channels, in which the one or more capillary channels of the third set each have a third cross-sectional area. A total volume of the first set, the second set, and the third set are approximately equal, where the first cross-sectional area, the second cross-sectional area, and the third cross-sectional area are different.

A mixing device of any of the above embodiments, in which the capillary channels has a tubular shape. The first set has a single capillary with a diameter X. The second set has a second number of capillaries where the second number of capillaries is about equal to a first inner diameter (ID) ratio to a fourth power. The first ID ratio is the diameter X divided by a diameter of a capillary channel in the second set. The third set has a third number of capillaries where the third number of capillaries is about equal to a second ID ratio to a fourth power. The second ID ratio is the diameter X divided by a diameter of a capillary channel in the third set. The second number of capillaries and third number of capillaries are each integer values.

A mixing device of any of the above embodiments, in which the mixer body is mounted within a housing. The housing having a first end and a second end. The first end being configured to be fluidically connected with an output from a pump and the second being configured to be fluidically connected with an input to a chromatography column.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements).

DETAILED DESCRIPTION OF EMBODIMENTS

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention. As used herein, the terms "about" or "approximately" for any numerical values or ranges indicate a suitable dimensional tolerance that allows the part or collection of components to function for its intended purpose as described herein.

Figure 1:
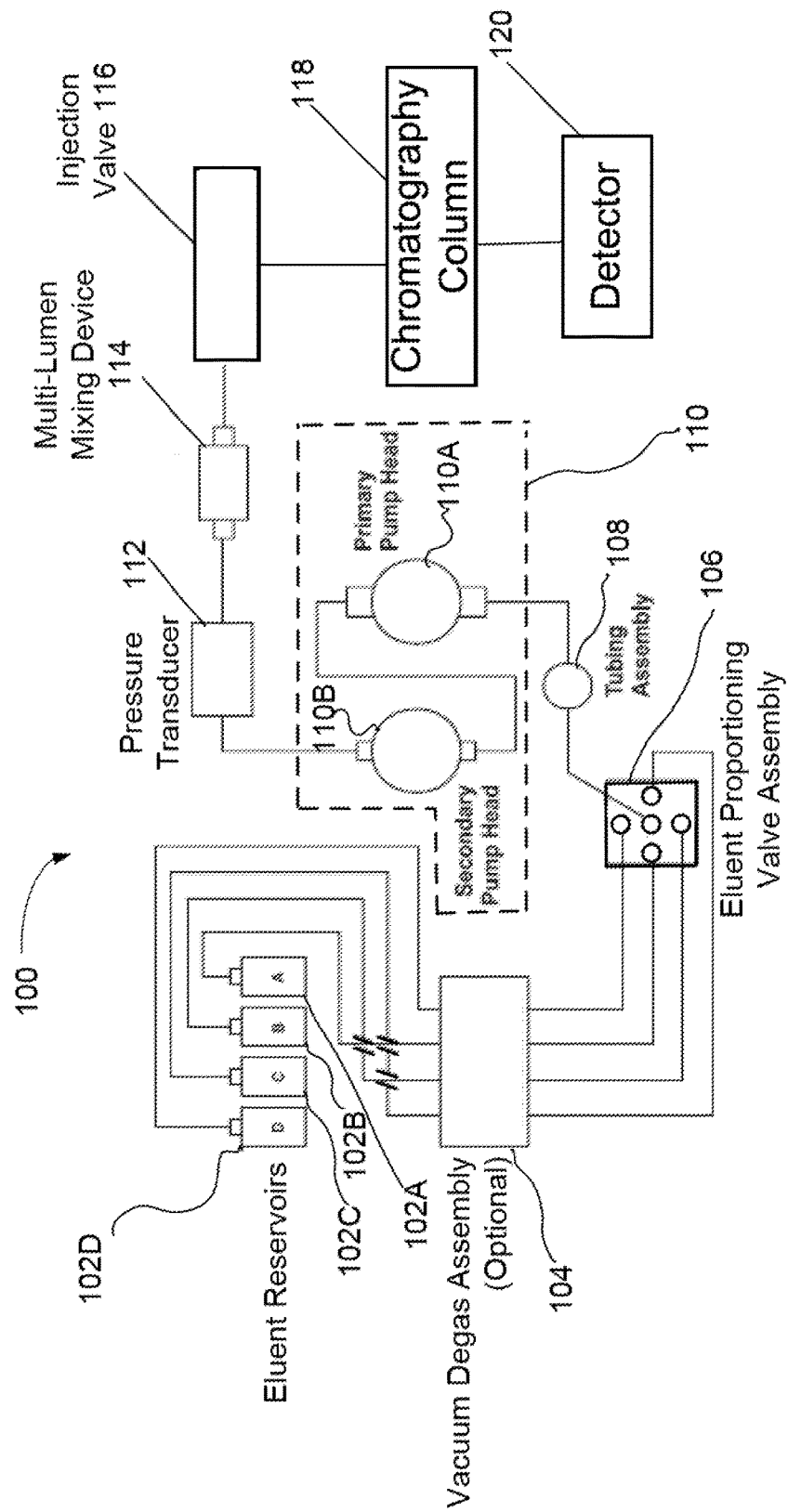
FIG. 1 illustrates a schematic of a chromatography system configured to perform a gradient elution with up to four different mobile phase reservoirs.

FIG. 1 illustrates a schematic of a chromatography system 100 configured to perform a gradient elution with up to four different mobile phase types. Chromatography system 100 can include four mobile phase reservoirs (102A, 102B, 102C, and 102D), an optional degas assembly 104, an eluent proportioning valve assembly 106, a tubing assembly 108, a pump 110, a pressure transducer 112, a multi-lumen mixing device 114, an injection valve 116, a chromatography column 118, and a detector 120. It should be noted that multi-lumen mixing device may be referred to as a multi-lumen mixer device, a mixing device, a gradient mixer, or a mixer. In an embodiment, multi-lumen mixing device is a static mixing device that does not use mechanical mixing within the mixer itself.

Figure 2:
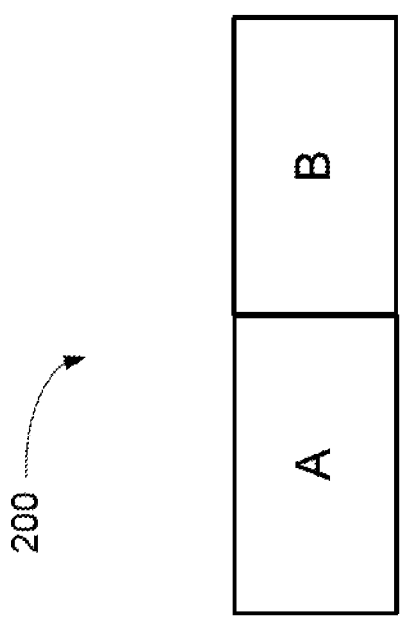
FIG. 2 illustrates a schematic of a heterogeneous solvent volume outputted from a proportioning pump where there are two different mobile phase plugs (A and B) immediately adjacent to each other.

The four mobile phase reservoirs (102A, 102B, 102C, and 102D) may each contain a different type of mobile phase type. Examples of typical mobile phase types used in gradient elution may include water, sodium carbonate, sodium hydroxide, sodium borate, methane sulfonic acid, acetonitrile, methanol, phosphate buffer, ammonium acetate, trifluoroacetic acid and combinations thereof. A mobile phase type may be a pure liquid or may be a solution having a salt concentration ranging from 1 mM to a 100 mM. The eluent proportioning valve assembly 106 can direct pump 110 to draw on one of the four mobile phase reservoirs for a predetermined time period and then switch to another mobile phase reservoir. Typically, the pump will draw upon each of the selected mobile phase types at least once during a piston cycle to form a plurality of adjoining solvent volumes. For example, two mobile phase reservoirs (102A and 102B) can be selected for the gradient elution. This will initially form a heterogeneous solvent volume (unmixed) containing solvent volume A and solvent volume B. Note that solvent volume A or B can be referred to as a plug of liquid that flows through a capillary such that there is not complete homogenization between the two plugs. Solvent volume A can be adjoining solvent volume B as illustrated in FIG. 2. The proportion of solvent A to solvent B depends on the timing in which eluent proportioning valve assembly 106 draws on reservoir 102A before switching to reservoir 102B. The heterogeneous solvent volume 200 is outputted from pump 110 and corresponds to an outputted solvent from one pump cycle. Note that the proportion of solvent A to solvent B can change with time. From the eluent proportioning valve assembly 106, the mobile phase flows to pump 110 via tubing assembly 108. As illustrated in FIG. 1, pump 110 has two parts that includes a primary pump head 110A and a secondary pump head 110B. The output of pump 110 flows to pressure transducer 112 and then to multi-lumen mixing device 114. After multi-lumen mixing device 114, the homogenous mobile phase flows through injection valve 116, chromatography column 118, and then to detector 120.

In an embodiment, multi-lumen mixing device 114 includes a volume greater than a total volume during one pump cycle. For example, if the total volume displacement of one pump cycle is 100 µL, selecting a composition of 1% mobile phase A and 99% mobile phase B results in a fluid segment consisting of 1 µL of mobile phase A followed by 99 µL of mobile phase B. In this embodiment with a 100 µL pump cycle volume, the mixer can preferably have a mixing volume of greater than 100 µL. In an embodiment, a volume of the mixer can be adjusted to be greater than the solvent volume of one piston cycle.

Figure 3:
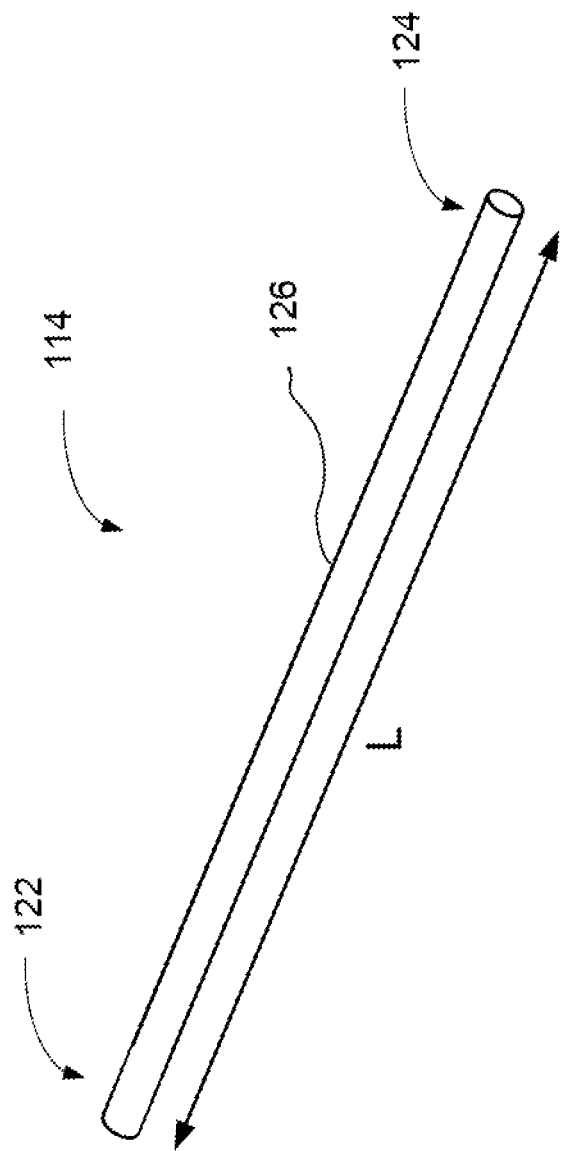
FIG. 3 is a simplified perspective view of a multi-lumen mixing device.

FIG. 3 is a perspective view of a multi-lumen mixing device 114. In an embodiment, the multi-lumen mixing device 114 may be tubular and have a length L of about 55 millimeters or about 105 millimeters. Tubular can refer to a hollow cylinder in the shape of a pipe. It should be noted that the length L is not limited to 55 or 105 millimeters and can be other values suitable for providing a volume that is greater than the volume of one pump cycle. The outer diameter (O.D.) of the multi-lumen mixing device 114 may range from about 2 millimeters to about 4 millimeters. Multi-lumen mixing device 114 includes a mixer body 126 having an inlet portion 122 and an outlet portion 124.

Figure 4:
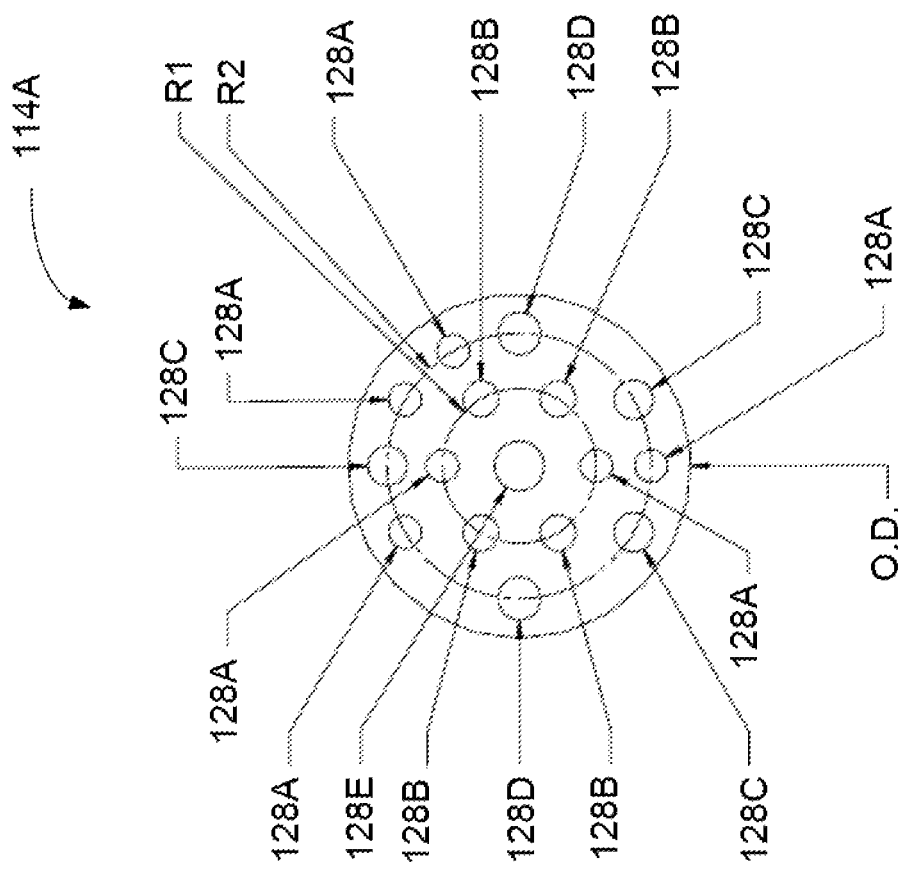
FIG. 4 is an end view of an embodiment of the multi-lumen mixing device.

As illustrated in FIG. 4, an embodiment of a multi-lumen mixing device 114A includes an array of capillary channels (128A, 128B, 128C, 128D, 128E) that are within the mixer body, in which each capillary channel has approximately a same length L. An inlet for each of the capillaries is proximate to the inlet portion 122 and an outlet for each of the capillaries is proximate to the outlet portion 124, in which the capillary channels of the array have five different cross-sectional areas. The term "set" is used to describe a group of one or more capillaries having approximately the same diameter. Accordingly, multi-lumen mixing device 114A of FIG. 4 has five sets, in which each set corresponds to a different cross-sectional area. Each one of the capillary channels (128A, 128B, 128C, 128D, 128E) can be classified to correspond to one of the five sets. In FIG. 4, there are 6 capillaries having a diameter of 0.0075 inches (128A, first set, 0.1905 mm), 4 capillaries having a diameter of 0.0083 inches (128B, second set, 0.2108 mm), 3 capillaries having a diameter of 0.009 inches (128C, third set, 0.2286 mm), 2 capillaries having a diameter of 0.0098 inches (128D, fourth set, 0.2489 mm), and 1 capillary having a diameter of 0.0114 inches (128E, fifth set, 0.2896 mm). Thus, FIG. 4 illustrates 5 different sets of capillaries that provide a total of 16 capillaries. In an embodiment, more than 5 different diameter sizes in capillary diameter can be used. In an embodiment, the mixer device may have 3 or more sets of capillaries, preferably 4 or more sets of capillaries, more preferably 5 or more sets of capillaries, and yet more preferably 6 or more sets of capillaries.

Referring to FIG. 4, capillary 128E can be aligned with the center point of the tube while the other capillaries (128A to 128D) can be aligned with a first radius R1 or a second radius R2. The first radius may be about 0.035 inches (0.889 mm) and the second radius may be about 0.06 inches (1.524 mm). In a variation to the embodiment shown in FIG. 4, the array of capillaries can be randomly distributed on the end face of the mixer body.

Figure 5:
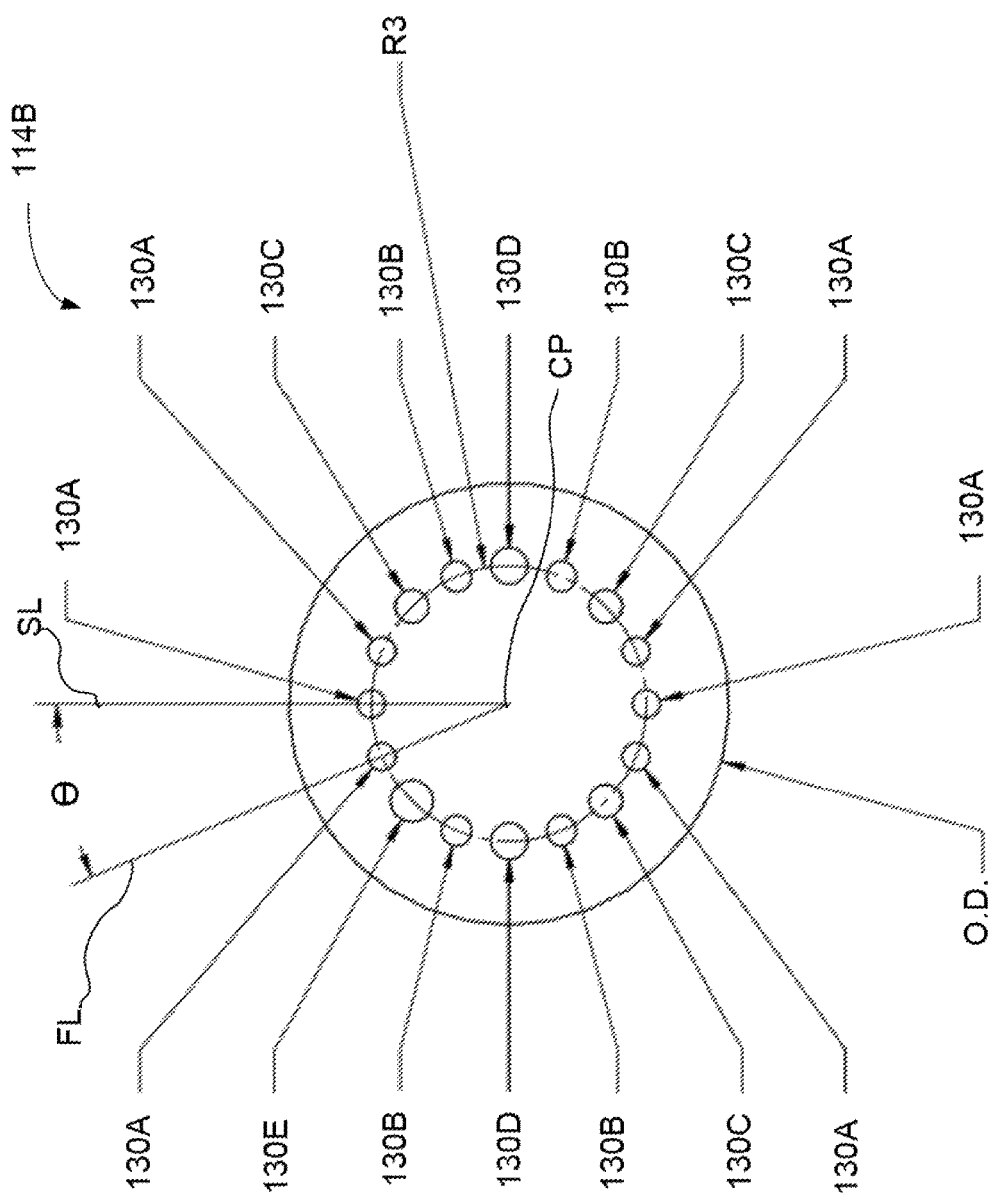
FIG. 5 is an end view of another embodiment of a multi-lumen mixing device.

As illustrated in FIG. 5, another embodiment of a multi-lumen mixing device 114B includes an array of capillary channels (130A, 130B, 130C, 130D, 130E) that are within the mixer body, in which each capillary channel has approximately a same length L. An inlet for each of the capillaries is proximate to the inlet portion 122 and an outlet for each of the capillaries is proximate to the outlet portion 124, in which the array of capillary channels have at least five different cross-sectional areas. In FIG. 5, there are 6 capillaries having a diameter of 0.01 inches (130A, first set, 0.254 mm), 4 capillaries having a diameter of 0.011 inches (130B, second set, 0.279 mm), 3 capillaries having a diameter of 0.012 inches (130C, third set, 0.305 mm), 2 capillaries having a diameter of 0.013 inches (130D, fourth set, 0.330 mm), and 1 capillary having a diameter of 0.0152 inches (130E, fifth set, 0.386 mm). Thus, FIG. 5 illustrates 5 different diameter sizes in capillary diameter and a total of 16 capillaries.

Referring to FIG. 5, the capillaries of multi-lumen mixing device 114B are circumferentially aligned with a third radius R3. The third radius may be about 0.0984 inches (2.50 mm) and the outer diameter of multi-lumen mixing device 114B is about 4 millimeters. The capillaries are evenly distributed along the third radius R3 where immediately adjacent capillaries form an angle θ. The angle θ is formed by a first line (FL) extending outwardly from a center point (CP) of the mixer body through a center point of a capillary (e.g., denoted as 130A in FIG. 5) and a second line (SL) extending outwardly from a center point (CP) of the mixer body through a center point of an immediately adjacent capillary (e.g., denoted as another 130A in FIG. 5) forms an angle θ. As shown in FIG. 5, the angle θ for multi-lumen mixing device 114B is about 22.5 degrees.

Multi-lumen mixing device may be constructed by an extrusion process. Resin can be extruded such that a tube is formed that has a plurality of capillary channels within the tube. In another embodiment, a bundle of capillary tubes could be inserted into a larger diameter tube with a potting compound to block flow in between the capillary tubes. In yet another embodiment, a bundle of capillary tubes could be inserted into a larger diameter tube without the potting compound to allow liquid flow through and around the capillary tubes where the flow through the interstitial space between the tubes acts as another flow path of the mixer assembly.

In an embodiment, the multi-lumen mixing device can be mounted within an inner diameter of a hollow tubing. The mounting may be done by a friction fit or the hollow tubing can be in the form of a heat shrink tubing. Under certain circumstances, the mounting in a hollow tubing can be done with an adhesive so long as care is taken to prevent adhesive obstruction of the capillary inlets and outlets. Both ends of the hollow tubing with a mounted multi-lumen capillary can be adapted to have fluidic fittings for incorporation into a chromatography system.

Now that the multi-lumen mixer has been described, the following will describe the process of using the multi-lumen mixer. In an embodiment, a multi-lumen mixer is fluidically connected with an output of a proportioning pump. The heterogeneous solvent volume outputted from the proportioning pump is inputted into the mixer. The heterogeneous solvent volume is then split it into a plurality of portions that flow into the capillary channels. The portions can flow through each of the capillary channels at different volumetric flow rates. When the various portions reach the end of mixer at different time periods, they are re-combined. The process of splitting the volume into portions and recombining creates the mixing process. The flow rates depend on the diameter of the capillary channel. A pressure drop in a capillary under laminar flow conditions is defined by Equation 1.

$$\Delta P = \frac{128 \, \mu L Q}{\pi d^4} \quad \text{(Eq. 1)}$$

The terms of Equation 1 are $\Delta P$=pressure loss, $\mu$=dynamic viscosity, L=length of the tube, Q=the volumetric flow rate, and d=diameter of the tube. The pressure drop creates a resistance to the liquid flow and slows down the flow of the liquid portions in the capillary tubes.

A simplistic example will be described with two capillary tubes where a first capillary has a diameter ($d=d_1$) and the second capillary has a diameter that is half of the first capillary ($d=d_1/2$). At a same volumetric flow rate (Q), the second smaller capillary will have a pressure drop that is 16 times greater (note that d is to the $4^{th}$ power in Eq. 1) than the larger first capillary. However, since the cross-sectional area of the smaller second capillary is one fourth that of the larger first capillary tube (note that the radius is $r=r_1$ for the first capillary, $r=r_1/2$ for the second capillary, and area=$\pi r^2$), the volumetric flow rate Q will need to be reduced by a factor of four in order to maintain equivalent linear velocity in the smaller second tube. So, at equivalent linear velocity, the pressure drop across the smaller tube will be four times greater than the larger diameter tube. Note that $\Delta P$ was determined using Eq. 1 based on the flow rate Q being 4 times less ($Q=Q_1/4$) and d being divided in half ($d=d_1/2$) to the $4^{th}$ power, which results in a four times greater pressure drop across the smaller tube. In the mixing application, the pressure applied to each capillary is identical since all capillaries are pressurized from a common source. Thus, the above relationship translates to the linear velocity of the smaller capillary being one fourth that of the linear velocity of the larger capillary when both are exposed to the same pressure.

In another scenario, there are 5 capillary tubes, all with identical lengths. One of the capillary tubes has a diameter $d_1$ and 4 of the capillary tubes have a diameter of $d_1/2$. The 4 smaller capillary tubes are plumbed in parallel to the larger tube. The 4 smaller tubes have a combined volume that is the same as the larger tube. The volumetric flow rate through one of the smaller tubes will be 4 times slower than the transit time through the larger tube. If two or more fluids to be mixed are allowed to enter the assembly of 5 tubes, the flow will be split between all of the 5 tubes in proportion to their pressure drop. In the example above, there will be a 4:1 split in the flow between the larger tube and the 4 smaller tubes with the majority of the flow passing thought the larger tube at four times the linear velocity. If the fluid to be mixed is co-mingled at the outlet of the tubing assembly, a modest amount of mixing will occur given the temporal differences between the transit times through the smaller ID tubing relative to the larger ID tubing. In this simple example mixing will not be very efficient because there are only two discrete transit times associated with the tubing assembly. Even so, an advantage of this approach is that the volumes of the tubes as well as their transit times can be calculated allowing the design and assembly of tubes with a suitable mixing volume. The mixing volume can be scaled for different flow rates by adjusting the tube length in proportion to the flow rates allows for direct scaling of the volume of the mixer.

In an embodiment, the mixer includes sets of tubes, all of identical length, where each set is of a nominally identical diameter such that the cumulative flow rate from each set of tubes is substantially the same. Substantially the same flow rates can describe two or more flow rates within 51% of each other, preferably 60%, more preferably 70%, yet more preferably 80%, and yet even more preferably 90% of each other. For example, consider the simplest case of two sets where the relative diameters are chosen to be X and 0.5 X. The following will describe how to determine the number of tubes of diameter 0.5 X and length Y that will, when taken together with the single tube of diameter X and length Y, produce the same volumetric flow rate at an identical applied pressure.

The ratio of pressure drops $\Delta P_r$ between two capillaries with diameters $d_1$ and $d_2$ is shown by Equation 2.

$$\Delta P_r = \frac{\frac{128 \mu L Q}{\pi d_1^4}}{\frac{128 \mu L Q}{\pi d_2^4}} = \frac{d_1^4}{d_2^4} \quad \text{(Eq. 2)}$$

In this case, where $d_2$ is half of the diameter of $d_1$, the pressure ratio can be represented by Equation 3.

$$\Delta P_r = \frac{d_1^4}{d_2^4} = \frac{1^4}{0.5^4} = 16 \quad \text{(Eq. 3)}$$

Since the pressure drop across the smaller capillary is 16 times larger than the larger capillary, the volumetric flow will be 1/16 that of the larger capillary if each capillaries exposed to the same pressure. It is possible to compensate for this lower volumetric flow rate by increasing the number of capillaries. In this example, choosing 16 capillaries will produce a flow rate that matches the volumetric flow rate of the larger capillary when the 16 capillaries are exposed to exactly the same pressure as the single larger capillary.

At the same time, the volume of the capillaries is given by Equation 4.

$$V = \frac{\pi d^2 L}{4} \quad \text{(Eq. 4)}$$

The ratio of the volumes ($V_r$) of the single larger capillary to the volume of the 16 smaller capillaries of the same length can be calculated using Equation 5.

$$V_r = \frac{\frac{\pi d_1^2 L}{4}}{\left(\frac{d_1^4}{d_2^4}\right) \pi d_2^2 L} = \frac{d_1^2}{\left(\frac{d_1^4}{d_2^4}\right) d_2^2} = \frac{1^2}{16(0.5)^2} = 4 \quad \text{(Eq. 5)}$$

Hence, while 16 capillaries of half the diameter exposed to the same pressure as a single larger will have an identical cumulative flow, the volume of these 16 capillaries will be four times larger than the volume of the single larger capillary. Thus, it will take four times longer for fluid to flow through the 16 smaller capillaries when compared to the transit time in the larger capillary.

In order to design a mixer with several sets of capillaries where each set has about the same volumetric flow, but different transit times, one can generalize the process described above. Using the above relationships, the following Table 1 lists the ID ratio and corresponding transit time ratio associated with sets of tubes that will have a volumetric flow rate identical to a single capillary of diameter X. Table 1 can be used to design mixers of different properties. Referring to Table 1, the "number of capillaries" refers to the number capillaries in a set that all have the same diameter where the diameter is smaller than the single capillary of diameter X. In Table 1, the "ID ratio" refers to the single capillary of diameter X divided by the diameter of one of the capillaries in the set. In Table 1, the "Transit time ratio ($T_r$)" represents a ratio indicating the amount of time needed for an analyte to travel through one of the capillaries in the set relative to the single capillary of diameter X. The transit time ratio ($T_r$) may also be referred to as the time-of-flight ratio through one of the capillaries in the set relative to the single capillary of diameter X.

For example, one could construct a mixer with four sets of capillaries consisting of one capillary with an ID of X and a time-of-flight of Y, 4 capillaries with an ID of 0.71X (i.e. X/1.41) and a time-of-flight of 2Y, 9 capillaries with an ID 0.58X (i.e. X/1.73) and a time-of-flight of 3Y, 16 capillaries with an ID ratio of 0.5X (i.e. X/2) and a time-of-flight of 4Y. In this example, there are a total of 30 capillaries based on the four sets of capillaries (1+4+9+16=30). Note that a time-of-flight of 2Y means that the time for solution to travel the set having 4 capillaries is twice as long as the travel time through the set having the single capillary having an ID of X.

TABLE 1

| Number of capillaries | ID ratio | Transit time ratio ($T_r$) |
|---|---|---|
| 2 | 1.19 | 1.41 |
| 3 | 1.32 | 1.73 |
| 4 | 1.41 | 2 |
| 5 | 1.50 | 2.24 |
| 6 | 1.57 | 2.45 |
| 7 | 1.63 | 2.65 |
| 8 | 1.68 | 2.83 |
| 9 | 1.73 | 3 |
| 10 | 1.78 | 3.16 |
| 11 | 1.82 | 3.32 |
| 12 | 1.86 | 3.46 |
| 13 | 1.90 | 3.61 |
| 14 | 1.93 | 3.74 |
| 15 | 1.97 | 3.87 |
| 16 | 2 | 4 |

It should be noted that trends were noted in Table 1 with the single larger capillary tube combined with a number of smaller capillary tubes (n) of the same length. The ID ratio can be calculated by taking the fourth root of n (i.e., $n^{1/4}$) and the transit time ratio can be obtained by taking square root of n (i.e., $n^{1/2}$).

Example 1

Figure 6:
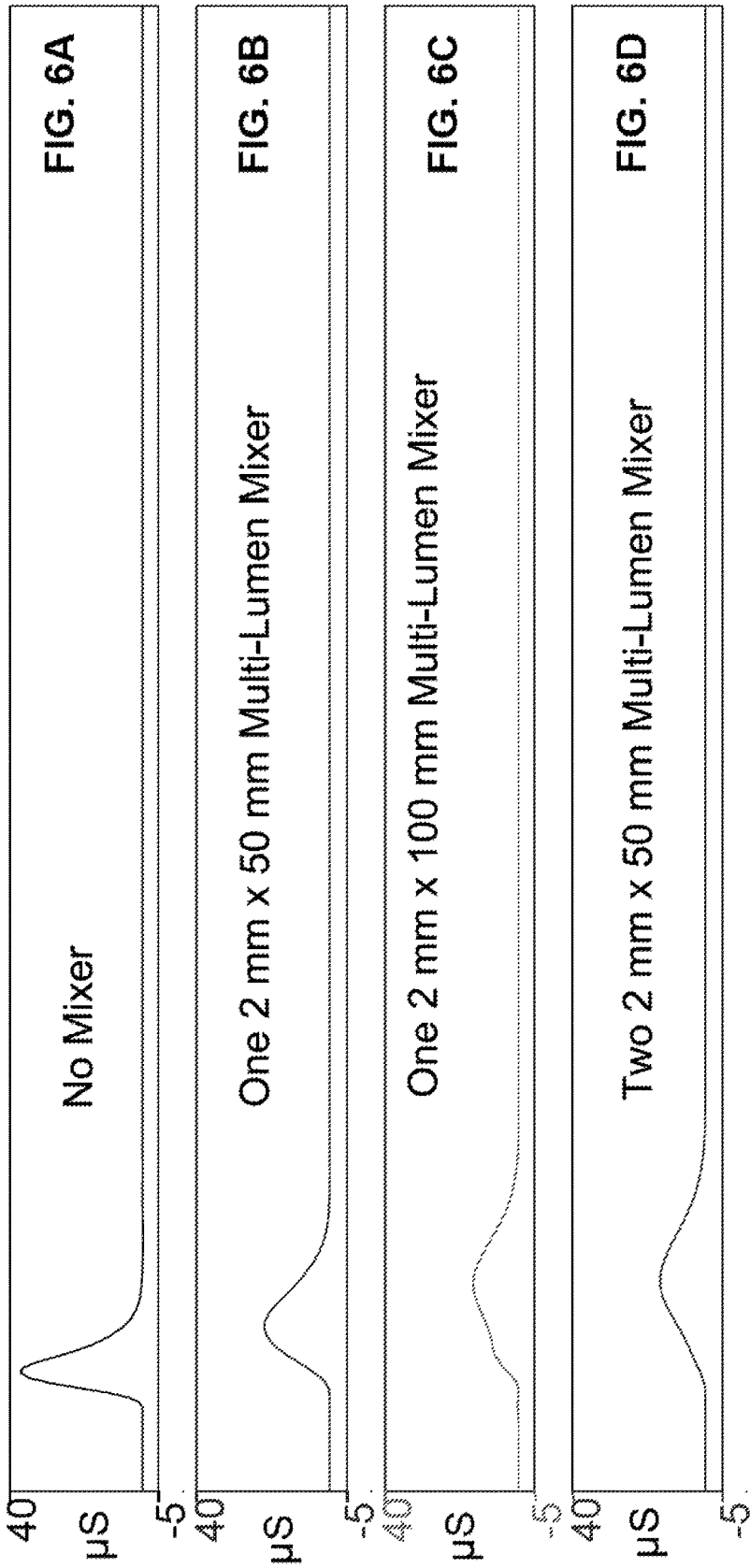
FIG. 6A illustrates a baseline test evaluation where a single liquid sample was injected with a sample loop and then detected at a conductivity detector without a mixing device and a chromatography column.
FIG. 6B illustrates a mixing test evaluation where a single liquid sample was injected, flowed through a multi-lumen mixing device (2 mm×50 mm), and then detected at a conductivity detector.
FIG. 6C illustrates a mixing test evaluation where a single liquid sample was injected, flowed through a multi-lumen mixing device (2 mm×100 mm), and then detected at a conductivity detector.
FIG. 6D illustrates a mixing test evaluation where a single liquid sample was injected, flowed through two multi-lumen mixing devices in series (2 mm×50 mm), and then detected at a conductivity detector.
Figure 10:
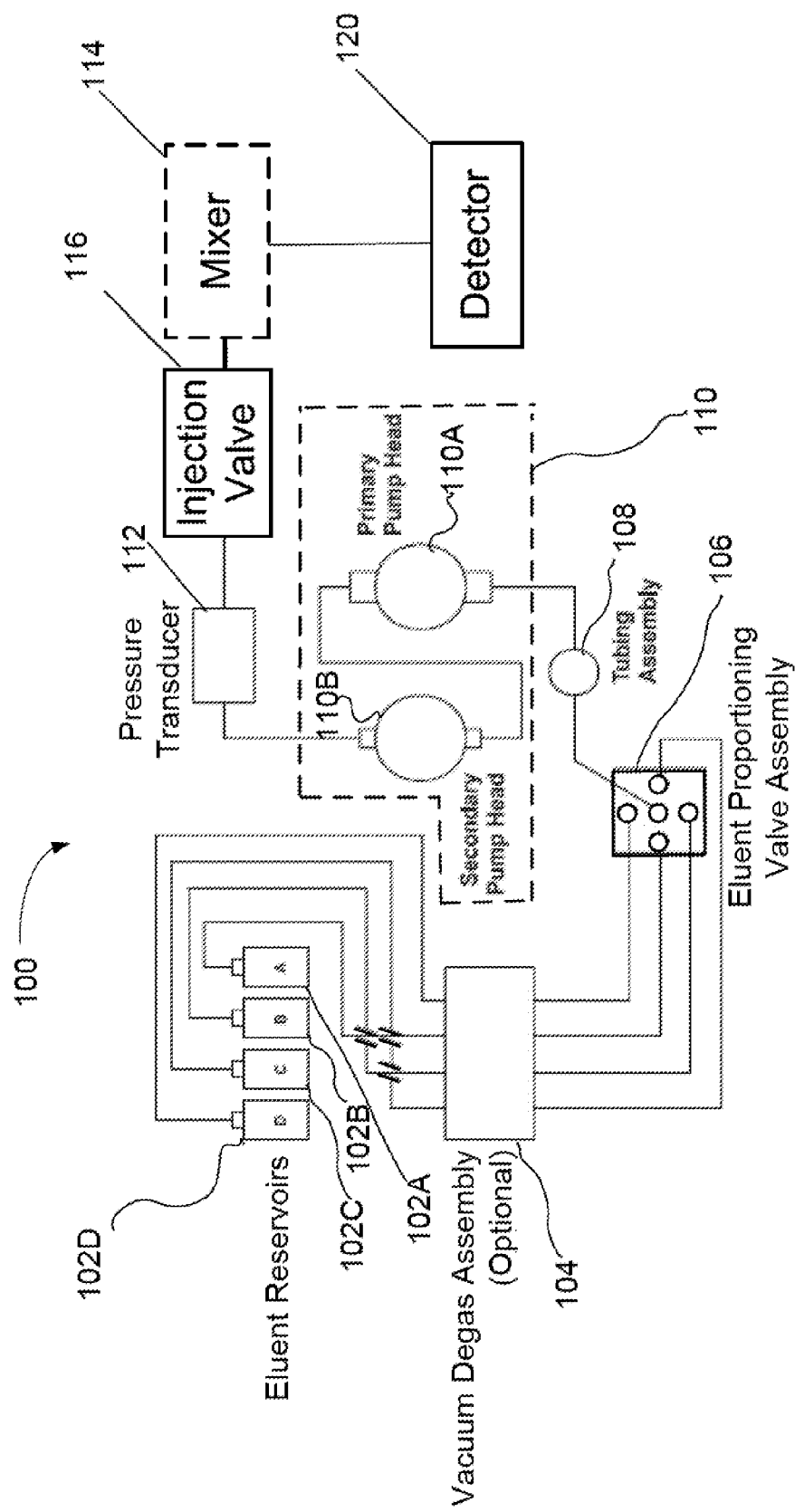
FIG. 10 illustrates a schematic of a test system configured to evaluate a performance of a mixer device.

A simulated chromatography system was set up similar to system 100 for evaluating the effectiveness of a mixer device. FIG. 10 shows a test system 1000 that does not have a chromatography column. In this Example, the mixing device 114 was not installed so that a background measurement can be done with an unmixed sample. A 5 μL sample containing 20 ppm NaNO$_3$ was injected into injection valve 116. Pump 102 flowed deionized water as the carrier at 1 mL per minute to move the sample plug out of injection valve 116 and then to a conductivity detector 120. FIG. 6A illustrates a single peak that was measured with the conductivity detector with no mixer being used.

Example 2

Test system 1000 was set up in accordance with FIG. 10. In this Example, the mixing device 114 was installed downstream of injection valve 116 and upstream of detector 120. The multi-lumen gradient mixer 114 was in accordance with embodiment 114A that was 2 mm×50 mm (O.D.×length, 30 μL volume) Note that test system 1000 evaluates the ability to homogenize a single plug of sample. A 5 μL sample containing 20 ppm NaNO$_3$ was injected into the system. Pump 102 flowed deionized water as the carrier 1 mL per minute to move the sample plug out of injection valve 116, to mixer 114, and then to conductivity detector 120. FIG. 6B illustrates a single peak that represents the sample volume mixed with the carrier in the multi-lumen mixing device (2 mm×50 mm) and measured at a conductivity detector. The mixing caused the sample peak to be attenuated and widened compared to the peak in FIG. 6A of Example 1.

Example 3

Test system 1000 was set up in accordance with FIG. 10. In this Example, the multi-lumen gradient mixer 114 was in accordance with embodiment 114A that was 2 mm×100 mm (O.D.×length, 60 μL volume) The mixer in this Example had the same O.D. and was twice as long as the one in Example 2. A 5 μL sample containing 20 ppm NaNO$_3$ was injected into the system. Pump 102 flowed deionized water as the carrier 1 mL per minute to move the sample plug out of injection valve 116, to mixer 114, and then to conductivity detector 120. FIG. 6C illustrates a peak that represents the sample volume mixed with the carrier in a multi-lumen mixing device (2 mm×100 mm) and measured at a conductivity detector. The mixing caused the peak to be attenuated and widened compared to the peak in FIG. 6B of Example 2. Thus, the mixer with a larger volume resulted in better mixing. It should be noted that an even larger volume mixer would provide incrementally better mixing than shown in FIG. 6C.

Example 4

Test system 1000 was set up in accordance with FIG. 10. In this Example, the multi-lumen gradient mixer 114 was two mixers plumbed in series in accordance with embodiment 114A that was 2 mm×50 mm (O.D.×length, 60 μL volume) The serially combined mixers in this Example had the same O.D. and the same effective length as the one in Example 3. A 5 μL sample containing 20 ppm NaNO$_3$ was injected into the system. Pump 102 flowed deionized water as the carrier 1 mL per minute to move the sample plug out of injection valve 116, to mixer 114, and then to conductivity detector 120. FIG. 6D illustrates a peak that was mixed with the carrier in two serially connected multi-lumen mixing devices (two, 2 mm×50 mm) and measured at a conductivity detector. The mixing caused the peak to be attenuated and widened in a manner similar to the peak in FIG. 6C of Example 3. Thus, the use of two mixers connected in a serial manner provided similar mixing compared to a single mixer with a volume similar to the total volume of two smaller mixers.

Example 5

Figure 7:
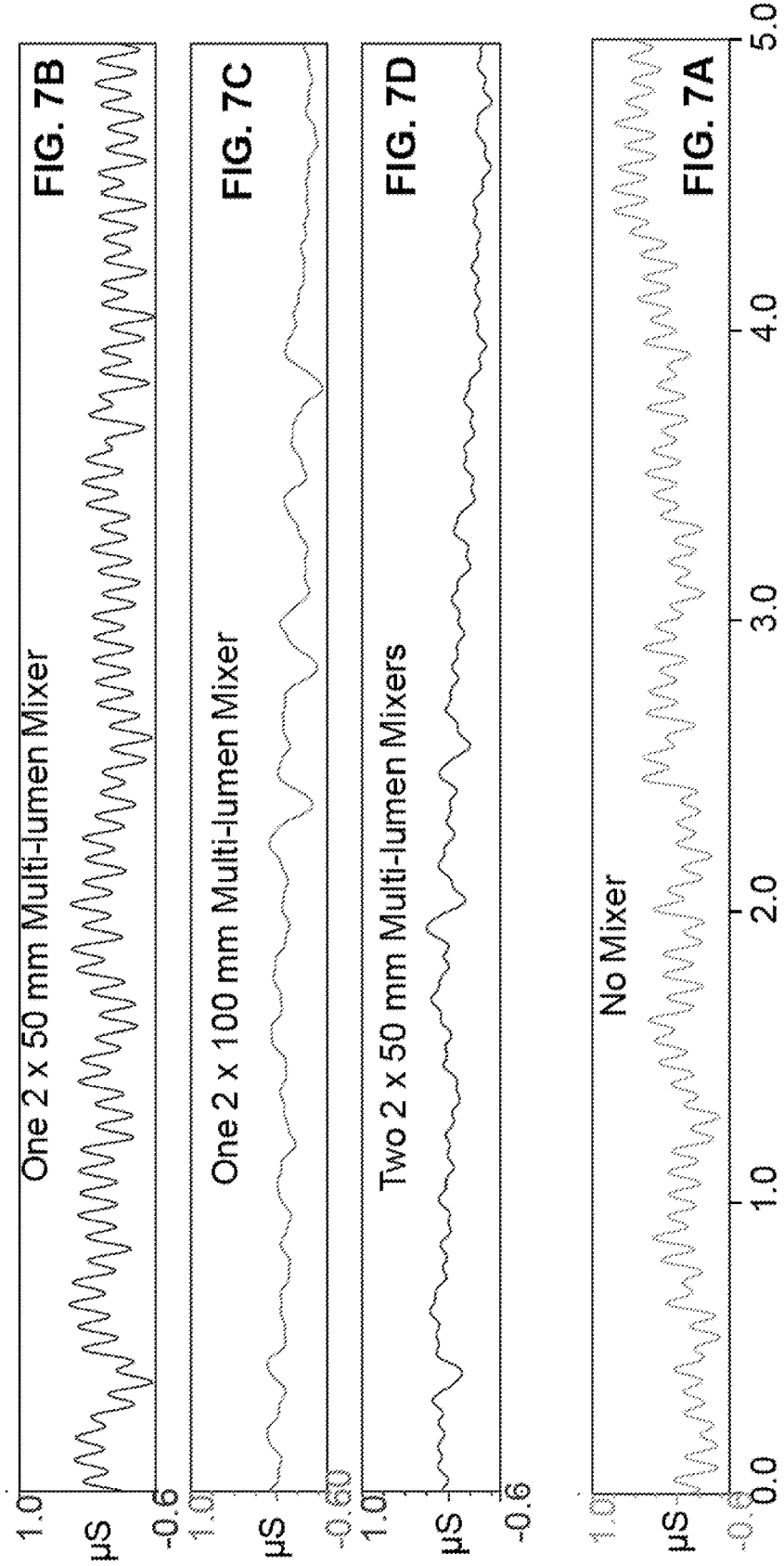
FIG. 7A illustrates a simulated chromatographic run where a series of heterogeneous solvent volumes pumped from a proportioning pump was flowed to a conductivity detector without an intervening mixing device. Each heterogeneous solvent volume contains a plug of deionized water immediately adjacent to another plug containing 1 mM $Na_2CO_3$.
FIG. 7B illustrates a simulated chromatographic run where a series of heterogeneous solvent volumes pumped from a proportioning pump was flowed through a multi-lumen mixing device (2 mm×50 mm), and then detected at a conductivity detector. Each heterogeneous solvent volume contains a plug of deionized water immediately adjacent to another plug containing 1 mM $Na_2CO_3$.
FIG. 7C illustrates a simulated chromatographic run where a series of heterogeneous solvent volumes pumped from a proportioning pump was flowed through a multi-lumen mixing device (2 mm×100 mm), and then detected at a conductivity detector. Each heterogeneous solvent volume contains a plug of deionized water immediately adjacent to another plug containing 1 mM $Na_2CO_3$.
FIG. 7D illustrates a simulated chromatographic run where a series of heterogeneous solvent volumes pumped from a proportioning pump was flowed through two multi-lumen mixing devices in series (2 mm×50 mm), and then detected at a conductivity detector. Each heterogeneous solvent volume contains a plug of deionized water immediately adjacent to another plug containing 1 mM $Na_2CO_3$.

A simulated chromatography system was set up similar to Example 1. In this Example, the mixing device 114 was not installed so that a background measurement can be done. In contrast to Examples 1 to 4 where a single sample was injected into injection valve 116, a series of heterogeneous solvent volumes was flowed through the system with the proportioning pump. Reservoir 102A contained deionized water and reservoir 102B contained 1 mM Na$_2$CO$_3$. Eluent proportioning pump was programmed to sample 90% from reservoir 102A and 10% from reservoir 102A during one pump cycle. The output for one cycle was about a 100 μL for one heterogeneous sample volume. A series of unmixed heterogeneous sample volumes were flowed at 1 mL per minute to a conductivity detector for detection. FIG. 7A illustrates a wavy saw-toothed baseline that was measured with the conductivity detector in which no mixer was used.

Example 6

The simulated chromatography system of Example 5 was tested with a mixing device 114. In this Example, the multi-lumen gradient mixer 114 was in accordance with embodiment 114A that was 2 mm×50 mm (O.D.×length, 30 μL volume. After the mixer, the carrier was flowed to a conductivity detector. FIG. 7B shows a wavy saw-toothed baseline that was similar to FIG. 7A. Note that the mixer in this Example has a 30 μL volume, which is much smaller than the output for one pump cycle (100 μL volume) of the proportioning pump.

Example 7

The simulated chromatography system of Example 5 was tested with another mixing device 114. In this Example, the multi-lumen gradient mixer 114 was in accordance with embodiment 114A that was 2 mm×100 mm (O.D.×length, 60 μL volume). After the mixer, the carrier was flowed to a conductivity detector. Note that the mixer in this Example had the same O.D. and was twice as long as the one in Example 6. FIG. 7C also shows wavy saw-toothed baseline that is attenuated compared to FIG. 7B indicating better mixing. Note that the mixer in this Example had a 60 μL volume, which is closer to the output volume for one pump cycle (100 μL volume) compared to Example 6.

Example 8

The simulated chromatography system of Example 5 was tested with a mixing device 114. In this Example, the multi-lumen gradient mixer 114 was configured as two mixer in series in accordance with embodiment 114A that was 2 mm×50 mm (O.D.×length, 60 μL volume). After the mixer, the carrier was flowed to a conductivity detector. Note that the two mixers in this Example had the same O.D. and the same total effective length as the one in Example 7. FIG. 7D also shows wavy saw-toothed baseline that is attenuated compared to FIG. 7B indicting better mixing. The mixing in FIGS. 7C and 7D appeared to have similar effectiveness. Note that the mixer in this Example and Example 7 used mixers that have a similar total volume of 60 μL.

Example 9

Figure 8:
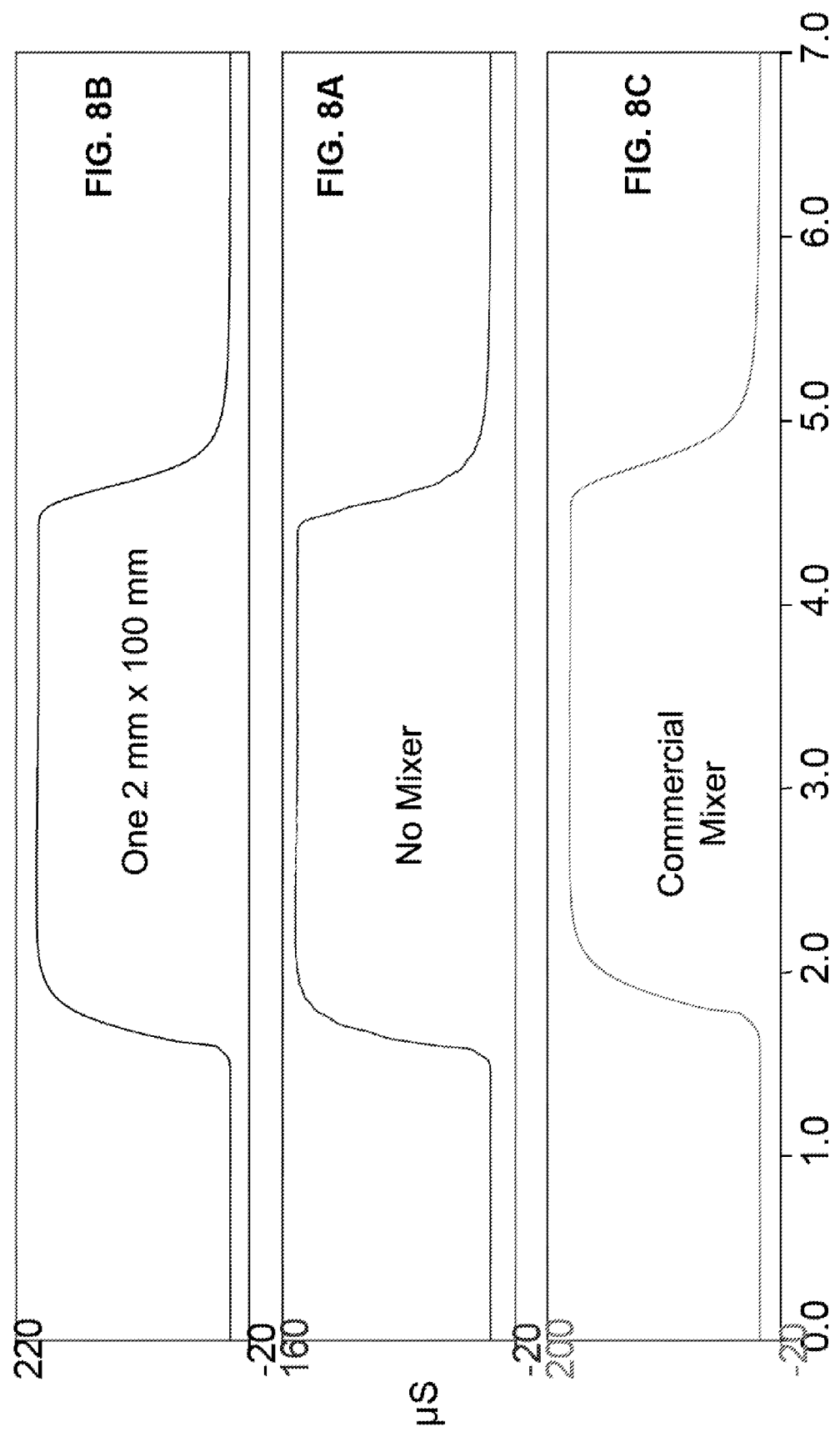
FIG. 8A illustrates a simulated chromatographic run where deionized water was flowed to a conductivity detector for about 1.5 minutes, switched to 1 mM $Na_2CO_3$ for about 3 minutes, and then washed out with deionized water, in which no mixing device was used.
FIG. 8B illustrates a simulated chromatographic run where deionized water was flowed through a multi-lumen mixing device (2 mm×100 mm) and then to conductivity detector for about 1.5 minutes. The flow was then switched to 1 mM $Na_2CO_3$ for about 3 minutes, and then switched back to deionized water to wash out the multi-lumen mixing device.
FIG. 8C illustrates a simulated chromatographic run where deionized water was flowed through a commercially available mixing device and then to conductivity detector for about 1.5 minutes. The flow was then switched to 1 mM $Na_2CO_3$ for about 3 minutes, and then switched back to deionized water to wash out the commercially available mixing device

A simulated chromatography system was set up similar to Example 5 with no mixing device. Reservoir 102A contained deionized water and reservoir 102B contained 1 mM $Na_2CO_3$. Eluent proportioning pump was programmed to pump 100% from reservoir 102A for 1 minute and then 100% from reservoir 102B for 3 minutes. FIG. 8A illustrates a relatively low conductance when deionized water was flowed through the system with an increase in conductance when $Na_2CO_3$ was flowed through the system until it reaches a plateau. Once the pump was switched back to deionized water, the conductance decreased. The time required for the conductance to reach a baseline value represents the wash through time for the system without a mixing device.

Example 10

The simulated chromatography system of Example 7 was tested with mixing device 114A that was 2 mm×100 mm (O.D.×length, 60 μL volume). Reservoir 102A contained deionized water and reservoir 102B contained 1 mM $Na_2CO_3$. Eluent proportioning pump was programmed to pump 100% from reservoir 102A for 1 minute and then 100% from reservoir 102B for 3 minutes. FIG. 8B illustrates a relatively low conductance when deionized water was flowed through the system with an increase in conductance when $Na_2CO_3$ was flowed through the system until it reaches a plateau. Once the pump was switched back to deionized water, the conductance decreased. The time required for the conductance to reach a baseline value represents the wash through time for the system with the mixing device.

Example 11

A simulated chromatography system similar to Example 7 was tested. In this Example a commercial mixing device was used. Reservoir 102A contained deionized water and reservoir 102B contained 1 mM $Na_2CO_3$. Eluent proportioning pump was programmed to pump 100% from reservoir 102A for 1 minute and then 100% from reservoir 102B for 3 minutes. FIG. 8C illustrates a relatively low conductance when deionized water was flowed through the system with an increase in conductance when $Na_2CO_3$ was flowed through the system until it reaches a plateau. Once the pump was switched back to deionized water, the conductance decreased. The time required for the conductance to reach a baseline value represents the wash through time for the system with the mixing device.

Figure 9:
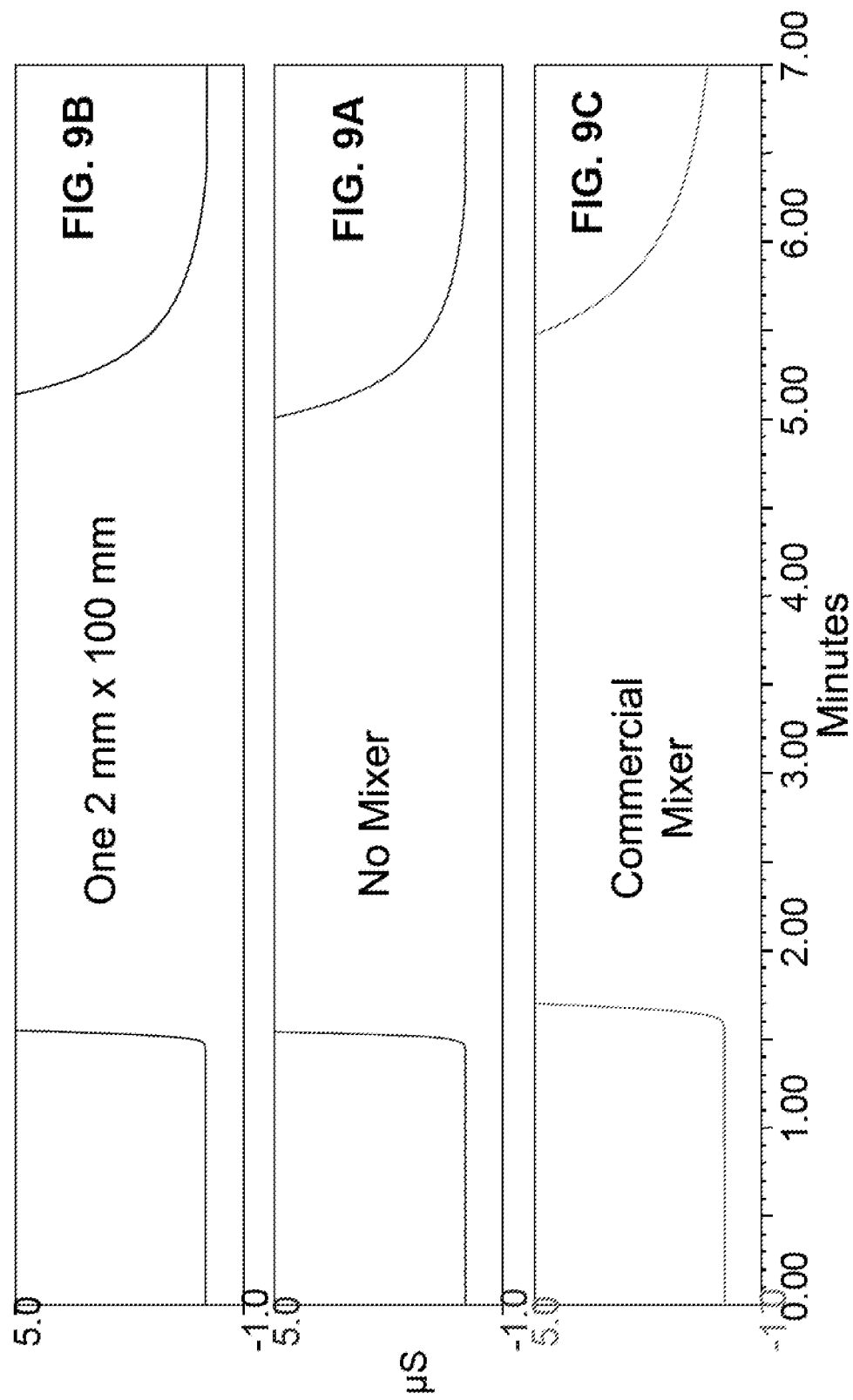
FIG. 9A illustrates an expanded view of the simulated chromatographic run of FIG. 8A.
FIG. 9B illustrates an expanded view of the simulated chromatographic run of FIG. 8B.
FIG. 9C illustrates an expanded view of the simulated chromatographic run of FIG. 8C.

FIGS. 9A, 9B, and 9C illustrate an expanded view of the simulated chromatographic run for FIGS. 8A, 8B, and 8C, respectively. FIG. 9B illustrates that the wash through time for mixing device 114A (2 mm×100 mm, 60 μL volume) was much faster than the commercial device and comparable to a system without a mixing device. Mixing device 114A resulted in less than 0.05 minute increase in the wash through time when compared to the same system without a mixing device. In addition, the wash through time of the commercial mixing device was substantially more than mixing device 114A. FIG. 9C shows that wash through of the carbonate eluent was still not complete after 0.75 minutes in the case of the commercial mixer.

While preferred embodiments of the present invention have been shown and described herein, it will be apparent to those skilled in the art that such embodiments are provided by way of example only. Numerous variations, changes, and substitutions will now occur to those skilled in the art without departing from the invention. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A method of mixing a heterogeneous solvent volume that includes a first plug of a first mobile phase type immediately adjacent to a second plug of a second mobile phase type, where the first mobile phase type and the second mobile phase type are different, the method comprising:
    pumping a first mobile phase type and a second mobile phase type with a pump to output the heterogeneous solvent volume;
    inputting the heterogeneous solvent volume into a multi-lumen mixing device at the first end face of the multi-lumen mixing device, the multi-lumen mixing device comprising:
        a mixer body comprising a first end face and a second end face;
        an array of capillary channels within the mixer body, in which each capillary channel substantially has a same length within a suitable dimensional tolerance, in which an inlet for each of the capillary channels of the array is at the first end face of the mixer body and an outlet for each of the capillary channels of the array is at the second end face of the mixer body in which the capillary channels of the array have at least three different cross-sectional areas;
    the array of capillary channels further comprising:
    a first set corresponding to one or more capillary channels, in which the one or more capillary channels of the first set each have a first cross-sectional area;
    a second set corresponding to a plurality of capillary channels, in which the plurality of capillary channels of the second set each have a second cross-sectional area; and
    a third set corresponding to a plurality of capillary channels, in which the plurality of capillary channels of the third set each have a third cross-sectional area, in which the first cross-sectional area, the second cross-sectional area, and the third cross-sectional area are different;
    outputting a mixture from the multi-lumen mixing device, in which the mixture contains the first mobile phase type and the second mobile phase type; and
    inputting the mixture into a chromatography column.

2. The method of claim 1 further comprising:
    separating a sample with the chromatography column; and
    detecting one or more analytes eluting off of the chromatography column.

3. The method of claim 1 further comprising:
increasing a proportion of the first mobile phase type with respect to the second mobile phase type as a function of time.

4. The method of claim 1, in which the array of capillary channels has a total volume that is equal to or greater than the heterogeneous solvent volume, in which the heterogeneous solvent volume comprises a volume of an outputted solvent from one pump cycle.

5. The method of claim 1, in which the capillary channels have a tubular shape.

6. The method of claim 1, in which the pump is a proportioning pump, the proportioning pump being configured to input a first mobile phase type from a first reservoir and to input a second mobile phase type from a second reservoir.

7. The method of claim 1, in which the multi-lumen mixing device is downstream of a sample injector.

8. The method of claim 1, in which the multi-lumen mixing device is upstream of a sample injector.

9. A multi-lumen mixing device comprising
a mixer body-comprising a first end face and a second end face;
an array of capillary channels within the mixer body, in which each capillary channel substantially has a same length within a suitable dimensional tolerance, in which an inlet for each of the capillary channels of the array is at the first end face and an outlet for each of the capillary channels of the array is at the second end face;
in which the array of capillary channels include:
a first set corresponding to one or more capillary channels, in which the one or more capillary channels of the first set each have a first cross-sectional area;
a second set corresponding to a plurality of capillary channels, in the plurality of capillary channels of the second set each have a second cross-sectional area; and
a third set corresponding to a plurality of capillary channels, in which the capillary channels of the third set each have a third cross-sectional area,
in which the first cross-sectional area, the second cross-sectional area, and the third cross-sectional area are different, in which the capillary channels have a tubular shape,
the first set has a single capillary with a diameter X,
the second set has a second number of capillaries where the second number of capillaries comprises a first inner diameter ratio to a fourth power, in which the first inner diameter ratio is the diameter X divided by a diameter of a capillary channel in the second set; and
the third set has a third number of capillaries where the third number of capillaries comprises a second inner diameter ratio to a fourth power, in which the second inner diameter ratio is the diameter X divided by a diameter of a capillary channel in the third set, in which the second number of capillaries and third number of capillaries are each integer values.

10. The mixing device of claim 9, in which the mixer body is mounted within a housing, the housing having a first end and a second end, the first end being configured to be fluidically connected with an output from a pump and the second end being configured to be fluidically connected with an input to a chromatography column.

* * * * *